United States Patent [19]

Wallace

[11] 4,130,617
[45] Dec. 19, 1978

[54] METHOD OF MAKING ENDOTRACHEAL TUBE CUFFS

[75] Inventor: Dean R. Wallace, Ft. Myers, Fla.

[73] Assignee: Airco, Inc., Montvale, N.J.

[21] Appl. No.: 865,825

[22] Filed: Dec. 30, 1977

[51] Int. Cl.² ............................................. B29C 17/07
[52] U.S. Cl. ................................... 264/528; 425/529
[58] Field of Search .................. 264/89, 94, 96–99, 264/DIG. 52; 425/526, 529

[56] References Cited

U.S. PATENT DOCUMENTS

| | | | |
|---|---|---|---|
| 3,333,036 | 7/1967 | Maurer et al. | 264/94 |
| 3,941,546 | 3/1976 | Hartig | 264/94 |

FOREIGN PATENT DOCUMENTS

| | | | |
|---|---|---|---|
| 226876 | 2/1960 | Australia | 264/94 |
| 50-26864 | 3/1975 | Japan | 264/94 |
| 15868 of | 1890 | United Kingdom | 264/94 |
| 850562 | 10/1960 | United Kingdom | 264/94 |

*Primary Examiner*—Jan H. Silbaugh
*Attorney, Agent, or Firm*—Roger M. Rathbun; Edmund W. Bopp; Larry R. Cassett

[57] ABSTRACT

A method is disclosed for making a cuff or balloon for use with an endotracheal tube by means of a cold parison blow molding process. The method may be utilized for large quantity production of such cuffs yet affords reliable control of the thickness throughout the cuff. In carrying out the method, a thermoplastic or other elastomeric tube of predetermined dimensions and elasticity is prestretched a predetermined amount in the longitudinal direction. The tube is positioned within a hollow mold or, for quantity production in a series of such molds, having the mold internal configuration in the general shape of the desired end balloon form. The mold or molds are vented to atmosphere. Pressure is applied to the interior of the tube and such predetermined pressure is retained within the tube. The tube and mold(s) are then heated such that the tube softens and expands under the pressure to assume internal configuration of the mold(s). A cooling cycle follows such that the tubing takes on a new memory in the expanded state. The expanded tube, now in the shape of the desired end cuff or balloon is removed from the mold and can then be assembled into the final product endotracheal tube by known means.

8 Claims, 10 Drawing Figures

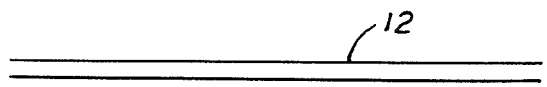
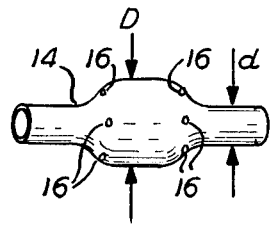
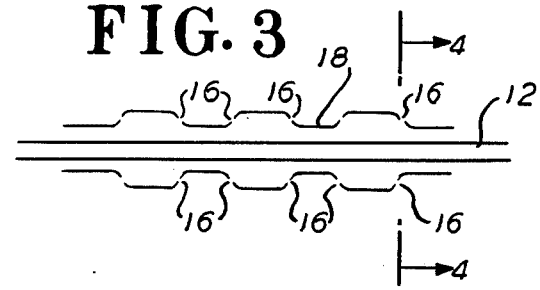
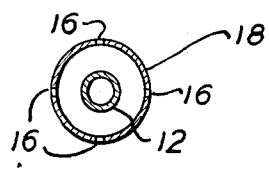
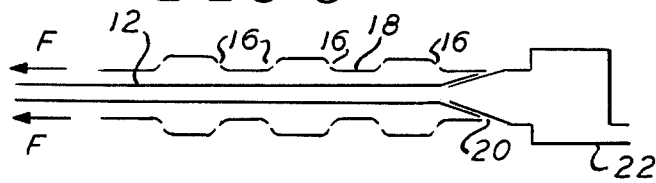
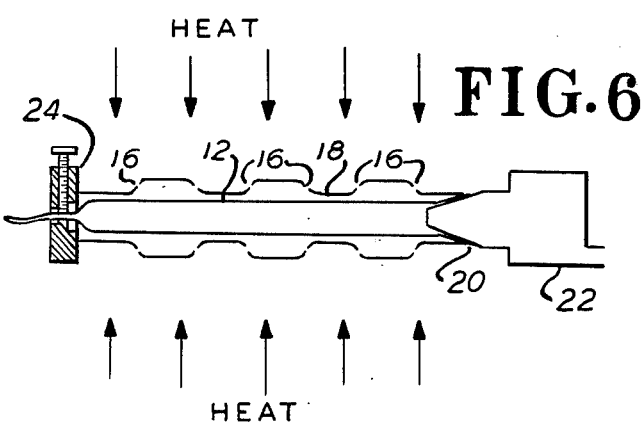
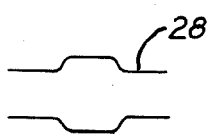
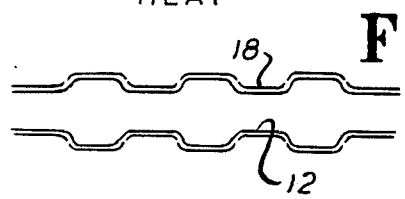
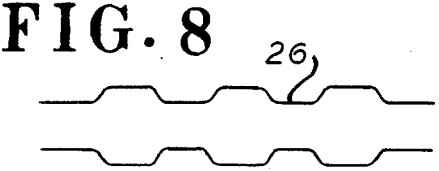
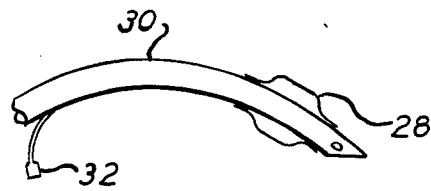

METHOD OF MAKING ENDOTRACHEAL TUBE CUFFS

BACKGROUND OF INVENTION

This invention relates to balloon-type catheters or endotracheal tubes which are adapted to be inserted into the trachea of a patient for introducing and removing respirable gases therefrom. Such catheters are well known to have inflatable cuffs or balloons which are inflated after the catheter is inserted to the desired position. The inflated cuff thereby seals against the internal walls, such as the trachea of a patient and can be deflated external of the patient in order to remove the catheter.

Such catheters are generally described in U.S. Pat. Nos. 3,901,246 and 3,625,793 where various catheters are described along with means of making the same.

One of the important components of such catheters is, of course, the inflatable cuff itself which must be controlled in thickness to prevent distortion upon inflation. The cuff must be sufficiently thick to contain gas under inflation pressure, yet be thin to conform to the patient's trachea and seal thereto. Also, due to the trend toward disposability of the catheters where each is designed for single patient use and thereafter discarded, the cuff, as well as the overall catheter, must be capable of being produced in large quantities at a low cost to the manufacturer.

In the manufacturing of such catheters, it is normal practice to produce the cuff independently and which is slipped over the main tube and secured in place over a suitable port for introducing air for inflation thereof. One such method of securing the cuff on the tube is disclosed in U.S. Pat. No. 3,625,793.

The cuff itself is therefore separately manufactured and presents its own unique problems in making the same. One currently used method of making such cuffs involves the dipping of a mold shaped in the profile of the desired cuff into plastisol. After a series of dippings, the plastisol is allowed to cure on the mold and is thereafter stripped from the mold. The process does produce cuffs of commercial quality, however, because the plastisol tends to drip on the mold during drying, the cuff thickness need not be uniform in each instance, and the cuffs themselves tend to be produced in differing thicknesses. In addition, a further difficulty with such process is that minute pinholes are essentially undetectable until the cuff is eventually assembled and secured to the trachea main tube. At this point the finding of such pinholes during quality control testing and rejection thereof renders useless a series of time-consuming steps previously taken in the overall manufacturing process. It would obviously be advantageous to detect such pinholes at the earliest possible step in the overall process so that the defective cuff could be most expeditiously rejected.

Other processes to manufacture cuffs have included blow-molding techniques where a mold consisting of two half molds are used and hot plastic compsition is introduced into the mold and blown by air pressure against the internal surface of the mold. The mold is then separated and the formed cuff is removed. Such process does, however, suffer from a defect in that a parting line is inevitably formed in the finished cuff as a result of the parting line of the two mold halves. The presence of such parting line on the finished cuff can cause difficulties in achieving a good gas seal between such cuff and the patient's trachea. Accordingly, preferably the parting line is removed from the cuff by further processing.

In accordance with the foregoing, a process is disclosed for manufacturing cuffs for endotracheal tubes or other catheters in which a cuff of predictable thickness is produced. The process is suited to mass production methods without sacrifice of quality and produces a cuff free of a parting line. Further, certain defects such as pinholes can, in certain instances, be detected early in the process and the cuff immediately rejected rather than have the opportunity to inspect the finished cuff only after assembly of the final endotracheal cuff.

SUMMARY OF INVENTION

Now, in accordance with the present invention, a method for manufacturing an inflatable balloon or cuff for an endotracheal tube or other catheter is described which produces a high quality, yet low cost cuff for assembly to a catheter tube. The method includes the use of a thermoplastic tubing of predetermined diameter, wall thickness and elasticity. The tubing is prestretched by stretching it along its longitudinal axis a predetermined minimum amount so that the resistance of the tubing to expansion in a radial direction is lessened. The prestretched tubing is positioned within a special mold having its internal surface shaped into the desired configuration of the eventual cuff and having suitable vents to accommodate the subsequent expansion of the tubing within the mold. The prestretching step may take place prior to positioning the tubing within the mold or, preferably, the tubing may be stretched while in position within the mold. The further description of the process will describe the mold in singular, however, it is understood that such mold, for high production purposes, may comprise a plurality of cavities serially positioned along such mold such that a plurality of cuffs are produced at the same time.

The tube is pressurized to a predetermined pressure depending upon the tube characteristics and the pressure is held within the tube. The tube and mold are then heated to a predetermined temperature, the heat acting to soften the thermoplastic tube and thus further reduce its resistance to expansion and distortion. The heat also serves to cause the thermoplastic material to lose its "memory". As the tube is heated, it expands out of its extruded tube profile and fills the internal surface of the mold, thus assuming the configuration of such surface. Cooling the mold and tube resets the memory of the thermoplastic material in its new expanded profile such that the cuff can be removed from the mold and it retains the desired cuff configuration. The final cuff configuration is thus ready to be joined to the endotracheal tube to make up the finished product.

Because the mold is a one piece unit, the finished cuff does not have a parting line, and thus a source of stress lines is eliminated as well as enhancing its appearance. Also, the cuff thickness is generally well controlled and its exact thickness predicted by knowledge of the dimensions of the thermoplastic tubing and the dimensions of the internal surface of the mold in which the tube is expanded. Thus, cuffs having a thickness of approximately 2 mils at their largest diameter and 6 mils at their smaller diameter are quite readily formed by this process. Accordingly, a cuff having a predetermined profile and predictable wall thickness can easily and inexpensively be manufactured.

DESCRIPTION OF THE DRAWINGS

The invention is diagrammatically illustrated, by way of example, in the drawings appended hereto, in which:

FIG. 1 is a schematic view of a thermoplastic tube used in the present invention;

FIG. 2 is a perspective view of a mold used in the invention to shape the cuff;

FIG. 3 is a cross-sectional view of a mold having a plurality of individual cuff shaped molds exemplified in FIG. 2 and showing a thermoplastic tube placed therein;

FIG. 4 is a cross-sectional view taken along the lines 4—4;

FIG. 5 is a schematic view showing the step the thermoplastic tube is prestretched along its longitudinal axis;

FIG. 6 is a schematic view showing the pressurized prestretched tube clamped in position in the mold and illustrating the heating step carried out in practicing the invention;

FIG. 7 is a schematic view showing the thermoplastic tube in its expanded condition within the plurality of molds after cooling and relief of the pressure;

FIG. 8 is a perspective view of a plurality of completed cuffs removed from the mold;

FIG. 9 is a perspective view of a finished cuff manufactured in accordance with the present invention; and FIG. 10 is a plan view of a completed endotracheal tube or catheter utilizing a cuff produced in accordance with this invention.

DETAILED DESCRIPTION OF THE INVENTION

Referring particularly to FIG. 1, there is shown a thermoplastic tube 12 upon which the invention is practiced to produce an endotracheal tube cuff or balloon. For reasons which will become apparent, the tube 12 is preferably a flexible, elastic thermoplastic material, such as polyvinyl chloride (PVC), however, other materials, including polyurethane could be used in practicing the invention. It is important that the tube wall thickness and elasticity be predetermined in order for the final cuff to be of predictable dimensions and flexibility required by the final commercial product. In particular, both properties of the tube 12 contribute to the wall thickness of the eventual completed cuff. As will later be explained, a further factor is the desired dimensional profile of the final cuff, since each of these parameters are related to the expansion of tube 12.

In FIG. 2 there is shown a containment means or mold 14, the inside of which is shaped in the particular profile or configuration desired for the final cuff. As will be seen, the mold 14 forms a larger diameter D which conforms to the outside diameter of the inflatable portion of the cuff and a small diameter d which conforms to that portion of a finished cuff that is adapted to be secured to the endotracheal main tube. The significance of predetermining these diameters and correlating the same with respect to the tube configuration and elasticity will be later explained.

The mold 14 is formed in a manner such that it is a single piece with a continuous, smooth inner surface, therefore, no parting lines appear on the final cuff as takes place when two half molds are used in present blow-molding procedures.

A number of procedures are available for producing the mold 14. One such procedure which provides excellent results entails forming a male mandrel in the desired shape of the final cuff. The male mandrel may be one of many appropriately selected metals of which aluminum is a suitable preferred choice. The mandrel is then plated by using a selective metallic material, such as nickel, to a desired thickness of about 0.030 inches. The mandrel is then removed by dissolving the same in a suitable vehicle, such as a caustic soda solution, thereby leaving the plated material having its internal surface shaped in the desired profile of the eventual cuff.

After the mold 14 is formed, vent holes 16 are drilled through the mold. The purpose of the vent holes 16 are to prevent entrapment of air within the mold during expansion of the thermoplastic tube 12. The vent holes 16 are preferably very minute, in the order of about 0.013 inches in diameter so that no markings appear on the finished cuff.

FIGS. 3 and 4 show a tube 12 inserted into a mold 18 having a plurality of serially arranged individual cuff molds which is utilized to increase the production rate of cuffs produced by practicing the method of this invention.

As may be seen in FIGS. 2, 3 and 4, the outside diameter of tube 12 must essentially expand to two different diameters to attain the configuration of the inside surface of the mold 18.

By determining these diameters to a desired configuration, the preferred wall thickness of the tube 12 can be predetermined. Obviously, one can, by calculation or experimentation, determine the wall thickness of the eventual expanded cuff by knowing the wall thickness of the original tube 12 and the desired end configuration.

The preferred wall thickness for PVC tubing used with this invention is from about 0.008 inches to 0.015 inches. It has been found that tubing of such wall thickness expands satisfactorily under the pressure and temperature conditions later explained. It should be noted, however, that tubing having a larger wall thickness could be used with corresponding increase in pressures. There is, of course, a point where the wall thickness of the tubing becomes too large and, after expansion to the desired cuff configuration, is not sufficiently flexible to be used on endotracheal tubes. Similarly, there is a lower limit of wall thickness of the tubes when, after expansion, the cuff wall thickness is too thin and thus the cuff is too delicate to resist handling or even in holding the pressure imposed upon it during normal use.

The prestretching step involved in carrying out the invention is shown schematically in FIG. 5. One end of the tube 12 is held tightly in position against mold 18, as shown, by catching the tube 12 between the mold 18 and an inwardly tapered nozzle 20 depending from air manifold 22.

While one end of the tube 12 is held in this fixed position, the free end is prestretched by exerting a force on the tube 12 acting in the direction of the arrows F of FIG. 5. The need for prestretching or some tension along the longitudinal axis of tube 12 was determined in developing this method of expanding cold thermoplastic tubing. The normal, non-prestretched tubing, when subjected to internal pressure to effect expansion of the same, tends to expand, in part, along its longitudinal axis.

Attempts to expand such tubing, therefore, resulted in erratic results due to the fact of longitudinal expansion. The expansion in the desired direction, i.e. radial, tended to be erratic and unpredictable inasmuch as the longitudinal expansion and radial expansion introduced complex resultant expansion. In instances, the expanded tubing resulted in areas of lines caused by overlapping of portions of the thermoplastic material in expansion under internal pressure.

The difficulty is eliminated through the introduction of a tensile force, as shown, to minimize longitudinal expansion. The tubing can effectively be expanded radially by use of internal pressure more readily under a constant tensile force than when no such force is present, It is believed that the reason for this result is that the tensile stretching distends the tubing longitudinally and thereby reduces the wall thickness of the tubing. Therefore, for a given internal pressure, the resistance to radial expansion also decreases. Since it is the radial expansion that is desired in carrying out this invention, the effect of the erratic longitudinal expansion is reduced to the point of being minimal or inconsequential. Thus, control can be directed to the radial expansion and effect of longitudinal expansions can be essentially eliminated.

The amount of prestretching is determined by the tube dimensions and characteristics, such as elasticity. It is estimated that the prestretching should result in an additional elongation of about 50 to 100%. Good results have been achieved using PVC tubing having a 0.010 inch wall thickness, an outside diameter of 0.265 inch and with an elasticity of 65 Durometer (Shore A scale) by prestretching the tubing to extend to a 80% elongation.

In carrying out the process, the tube 12 is maintained in its prestretched condition by carrying out the stretching step illustrated in FIG. 5 followed by clamping the open end with a suitable clamp 24 shown in FIG. 6. By positioning the clamp 24 abuting the end of mold 18 so that the tube 12 cannot shrink inwardly within mold 18, prestretch of the tube 12 is retained.

As a further step in the overall process, pressure is applied to the inside of the tube 12. The pressure may be supplied by causing air to be forced into the tube 12 from the air manifold 22 which may readily be supplied by a normal, valved, regulated control air supply. As will be seen, the use of a mainfold 22 can allow the simultaneous processing of a plurality of molds 18 operating from the same manifold 22. With PVC tubing of wall thickness of about 0.010 inches, air pressure in the order of about 6 inches of mercury is considered sufficient to provide good results in carrying out this process. The actual pressure required depends upon the tube wall thickness, its elasticity and the desired end configuration.

As further shown in FIG. 6, the mold 18 containing the tube 12 is heated while retaining pressure within the tube 12 and while being retained in its stretched condition.

The heat is applied to decrease the distortion resistance of the thermoplastic material of tube 12. The tube 12 becomes more elastic and its resistance to expansion from the internal pressurization decreases to the point where the tube 12 expands and blows up inside the mold 18, thereby fitting itself to the internal surface of the mold 18 to assure that configuration. With PVC tubing it has been found sufficient to heat the tube 12 and mold 18 at a temperature of about 250°-275° F. for a period of about five minutes.

The application of heat to the thermoplastic material causes that material to lose its memory as it expands to the new profile offered by the internal surface of mold 18.

To reset the memory of the thermoplastic material in its new configuration, the mold and expanded tubing is removed from the heat and allowed to cool to room temperature. The cooling again sets the molecular structure of the thermoplastic material so that it remains set in its expanded profile. The cooling cycle takes place while retaining pressure within the now-expanded profile.

At the end of the cooling cycle, the pressure is relieved and the formed cuffs are set with their new memory within the mold 18 and now assuming that internal configuration as shown in FIG. 7. In FIG. 8, a string of formed cuffs, shown as 26, is pulled from the mold. The string 26 can then easily be cut into individual cuffs 28, shown in FIG. 9.

In FIG. 10 there is shown a completed endotracheal tube having affixed thereon a cuff 28 produced in accordance with this invention.

The cuff 28 may be affixed and sealed to the exterior of the main trach tube 30 by known means. A small lumen, not shown, which can be formed in the wall of the main tube 30 extends from the inflating valve 32 to the interior of cuff 28 whereby air can be introduced by known means, such as by a syringe through a valve 32 described in U.S. Pat. No. 3,901,246 to the interior of cuff 28 to inflate the same or can be withdrawn therefrom to deflate the same.

There is thus provided an easy yet very effective method of forming a cuff for use with an endotracheal tube which may be utilized to produce, in high quantity, excellent quality cuffs having predictable wall thickness and a smooth continuous exterior finish. Because the cuffs are formed by this process having pressurized interior, there is further a likelihood that pinholes may become readily apparent by pressure leaks and resultant collapse of the formed cuff, thus providing an indication of a cuff rejection well in advance of actual testing of an assembled cuff.

It will be understood that the scope of the method of this invention is not limited to the particular steps or materials disclosed herein, by way of example, but only by the scope of the appended claims.

I claim:

1. A method of producing cuffs for endotracheal tubes comprising the steps of:
    (a) providing an elastomeric thermoplastic tube of predetermined elasticity, diameter and wall thickness;
    (b) positioning the tube within a vented hollow mold having an internal configuration in the shape of at least one desired cuff;
    (c) prestretching the tube a predetermined amount along its longitudinal axis, and maintaining said prestretch throughout steps (d) and (e) to minimize longitudinal expansion during pressurizing;
    (d) pressurizing the interior of said tube while contained within said mold and retaining said pressure within said tube throughout step (e);
    (e) heating the mold and the tube contained within, at a temperature sufficient to soften said tube and cause it to expand into said mold, thereby forming a cuff;
    (f) removing the heat from the mold and tube to allow said mold and tube to return to ambient temperature; and (g) removing the at least one formed cuff from the mold.

2. A method of producing cuffs for endotracheal tubes as described in claim 1 wherein said stretching comprises elongating said tube to about at least 50% increase in length.

3. A method of producing cuffs for endotracheal tubes as described in claim 1 wherein said positioning the tube within a vented hollow mold comprises positioning the hole within a mold comprising a plurality of endotracheal cuff shaped molds.

4. A method of producing cuffs for endotracheal tubes as described in claim 1 wherein said elastomers thermoplastic tube is polyvinyl chloride having an elasticity of about 65 Durometer (Shore A scale).

5. A method of producing cuffs for endotracheal tubes as described in claim 4 wherein said heating step takes place at a temprature of between about 250° F. to about 275° F.

6. A method of producing cuffs for endotracheal tubes as described in claim 4 wherein said pressurizing the interior of said tube comprises forcing a gas into said tube to attain a pressure of 6 inches of mercury.

7. A method of producing cuffs for endotracheal tubes comprising the steps of:
(a) providing an elastomeric thermoplastic tube of predetermined elasticity, diameter and wall thickness;
(b) positioning the tube within a vented hollow mold having an internal configuration in the shape of the desired cuff;
(c) forcing a tapered gas nozzle into one end of said tube to sealingly engage said tube against the interior of one end of the mold;
(d) while maintaining said sealing engagement of step (c), stretching the other end of said tube a predetermined amount along the longitudinal axis to mimimize longitudinal expansion during pressurizing;
(e) clamping the stretched tube end to maintain the tube in the stretched condition;
(f) pressurizing the interior of said tube while contained within said mold by gas pressure introduced through said tapered gas nozzle;
(g) retaining said pressure within said tube throughout step (h);
(h) heating the tube at a temperature sufficient to soften said tube and cause it to expand into said mold, thereby forming at least one cuff;
(i) removing the heat from the tube to allow said tube to return to ambient temperature; and
(j) removing the at least one formed cuff from the mold.

8. A method of producing cuffs for endotracheal tubes as described in claim 7 wherein said heating step takes place at a temperature between about 250° F. to about 275° F.

* * * * *